United States Patent
Yang

(10) Patent No.: US 9,636,272 B2
(45) Date of Patent: May 2, 2017

(54) THERAPEUTIC APPLIANCE

(71) Applicant: Cheng-Chuan Yang, Taichung (TW)

(72) Inventor: Cheng-Chuan Yang, Taichung (TW)

( * ) Notice: Subject to any disclaimer, the term of this patent is extended or adjusted under 35 U.S.C. 154(b) by 392 days.

(21) Appl. No.: 14/250,387

(22) Filed: Apr. 11, 2014

(65) Prior Publication Data

US 2014/0221880 A1  Aug. 7, 2014

Related U.S. Application Data

(63) Continuation-in-part of application No. 13/919,988, filed on Jun. 17, 2013, now Pat. No. 9,271,865, which
(Continued)

(51) Int. Cl.
*A61H 23/02* (2006.01)
*A61F 7/00* (2006.01)
(Continued)

(52) U.S. Cl.
CPC ........... *A61H 23/02* (2013.01); *A61F 7/0085* (2013.01); *A61F 7/02* (2013.01); *A61H 23/0263* (2013.01); *A61F 2007/0003* (2013.01); *A61F 2007/0024* (2013.01); *A61F 2007/0025* (2013.01); *A61F 2007/0042* (2013.01); *A61F 2007/0054* (2013.01); *A61F 2007/0076* (2013.01); *A61F 2007/0228* (2013.01); *A61F 2007/0279* (2013.01); *A61H 2201/0157* (2013.01); *A61H 2201/0207* (2013.01); *A61H 2201/0214* (2013.01); *A61H 2201/0228* (2013.01); *A61H 2201/0242* (2013.01); *A61H 2201/164* (2013.01); *A61H 2201/1604* (2013.01); *A61H 2201/165* (2013.01);
(Continued)

(58) Field of Classification Search
CPC .... A61H 23/00; A61H 23/02; A61H 23/0245; A61H 23/0254; A61H 23/0263; A61H 2023/0272; A61H 2201/02; A61H 2201/0207; A61H 2201/0214; A61H 2201/0242; A61H 2201/0264; A61H 2201/1654; A61F 2007/0225; A61F 2007/0228; A61F 7/02; A61F 7/0053; A61F 2007/0054; A61F 2007/0056; A61F 2007/0071; A61F 7/0085
See application file for complete search history.

(56) References Cited

U.S. PATENT DOCUMENTS 4,125,112 A * 11/1978 Weihs ............... A61H 23/04
601/46
4,574,787 A 3/1986 Jacobs
(Continued)

*Primary Examiner* — Justine Yu
*Assistant Examiner* — Michael Tsai
(74) *Attorney, Agent, or Firm* — Rosenberg, Klein & Lee

(57) ABSTRACT

A therapeutic appliance includes a water pack, at least one massaging finger, a recirculating water system and a thermoelectric device. The massaging finger has a vibrator disposed on the water pack to exciting liquid in the water pack for massaging a body portion to be massaged. The recirculating water system has a container and a conduit connecting the container and the water pack such that the liquid is permitted to circulate between the container and the water pack. In addition, the thermoelectric device is disposed in the container of the recirculating water system for heating or cooling the liquid.

6 Claims, 10 Drawing Sheets

Related U.S. Application Data is a continuation-in-part of application No. 13/044,508, filed on Mar. 9, 2011, now Pat. No. 8,491,505.

(51) Int. Cl.
*A61F 7/02* (2006.01)
*A61N 7/00* (2006.01)

(52) U.S. Cl.
CPC ............ *A61H 2201/1623* (2013.01); *A61H 2201/1654* (2013.01); *A61H 2205/022* (2013.01); *A61H 2205/024* (2013.01); *A61H 2205/081* (2013.01); *A61H 2205/102* (2013.01); *A61N 7/00* (2013.01)

(56) References Cited

U.S. PATENT DOCUMENTS

| | | | | |
|---|---|---|---|---|
| 5,072,724 | A | * 12/1991 | Marcus | A61H 23/0245 601/148 |
| 5,806,335 | A | * 9/1998 | Herbert | A61F 7/10 607/114 |
| 2004/0249427 | A1 | * 12/2004 | Nabilsi | A61F 7/0085 607/104 |
| 2012/0253243 | A1 | * 10/2012 | Ikeyama | A61H 23/0263 601/46 |

\* cited by examiner

THERAPEUTIC APPLIANCE

CROSS-REFERENCE TO RELATED APPLICATION

This is a continuation-in-part of co-pending application Ser. No. 13/919,988, filed on Jun. 17, 2013, now Pub. No 2013/0281893, which is a continuation-in-part of application Ser. No. 13/044,508, filed on Mar. 9, 2011, now U.S. Pat. No. 8,491,505.

BACKGROUND OF THE INVENTION

1. Field of the Invention

The present invention relates to a therapeutic appliance and more particularly to a therapeutic appliance with a recirculating water system to apply hot or cold liquid to a water pack for massaging a human body.

2. Description of the Related Art

Devices for therapeutic massage of portions of human body are well known, such as evidenced in U.S. Pat. No. 4,574,787. This patent provides an acupressure apparatus for applying vibrational pressure evenly to a plurality of preselected points on a shaped portion of a living body. The apparatus includes a rigid housing and a flexible membrane fixedly secured to said housing so as to form an enclosed chamber between said housing and said flexible membrane for containing a liquid when disposed within said chamber. Moreover, the apparatus farther comprises means for heating said liquid, and therefore the apparatus can simultaneously deliver heat as well as pressure. The heating, means is illustrated in the form of a heater mounted directly on the mask. The heater is electrically connected to a step down transformer and includes a heating element disposed in the liquid and a thermostat similarly disposed in the liquid. The heater acts to achieve a preselected temperature for liquid. However, danger or discomfort (including psychological) could be caused to the user because the heater is right on the mask and very close to the body to be massaged.

SUMMARY OF THE INVENTION

It is an objective of the present invention to provide a safer therapeutic appliance which utilizes a recirculating water system to apply hot or cold liquid to a water pack for massaging. In particular, a thermoelectric device is employed in a container of the recirculating water system, far from the water pack to ensure safety of the human body.

To achieve the foregoing objectives, the therapeutic appliance generally includes a water pack, at least one massaging finger, a recirculating water system and a thermoelectric device. The massaging finger has a vibrator which is disposed on the water pack to excite liquid inside the water pack for massaging a body portion to be massaged. The recirculating water, system includes a container and a conduit connecting the container and the water pack such that the liquid is permitted to circulate between the container and the water pack. The thermoelectric device is disposed in the container of the recirculating water system for heating or cooling the liquid.

Preferred embodiments of the invention may have the following additional characteristics, either alone or in combination:

The water pack has one side to be in contact with the body portion and the opposite side on which the vibrator is mounted.

The therapeutic appliance further comprises a rigid covering generally placed over the water pack as well as the massaging finger.

The covering is shaped to form a receptacle to receive the vibrator. In one example, the massaging finger further includes a spring interposed in between the receptacle and the vibrator.

In another example, the massaging finger further includes a buffering base and a plurality of flexible ribs. Each of the ribs has one end extending from a periphery of the buffering base and the other end attached to an internal wall surface of the water pack such that the ribs are arranged in a shape generally conforming to a contour of the vibrator.

Further benefits and advantages of the present invention will become apparent after a careful reading of the detailed description with appropriate reference to the accompanying drawings.

BRIEF DESCRIPTION OF THE DRAWINGS

In order that the present invention may be more fully understood, it will now be described, by way of example, with reference to the accompanying drawing in which.

DETAILED DESCRIPTION OF EMBODIMENTS

Figure 1:
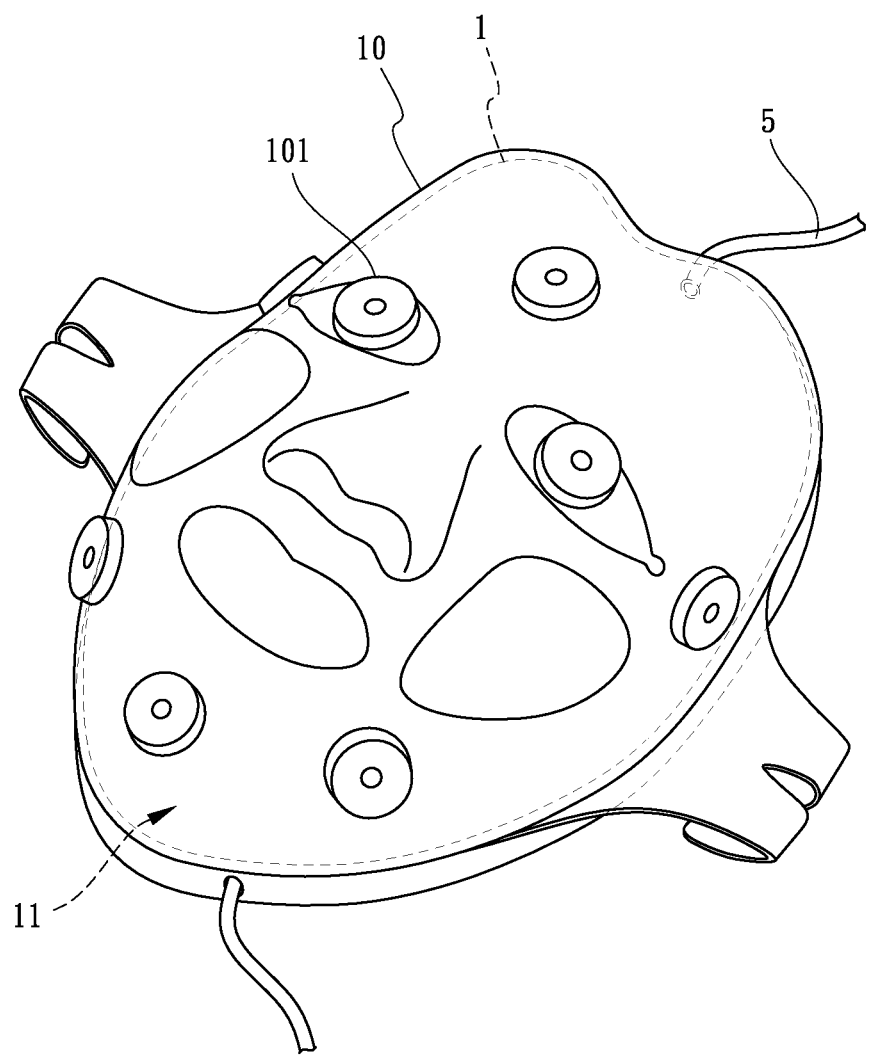
FIG. 1 is a perspective view of a mask of a therapeutic appliance in accordance with the preferred embodiment of the present invention.
Figure 2:
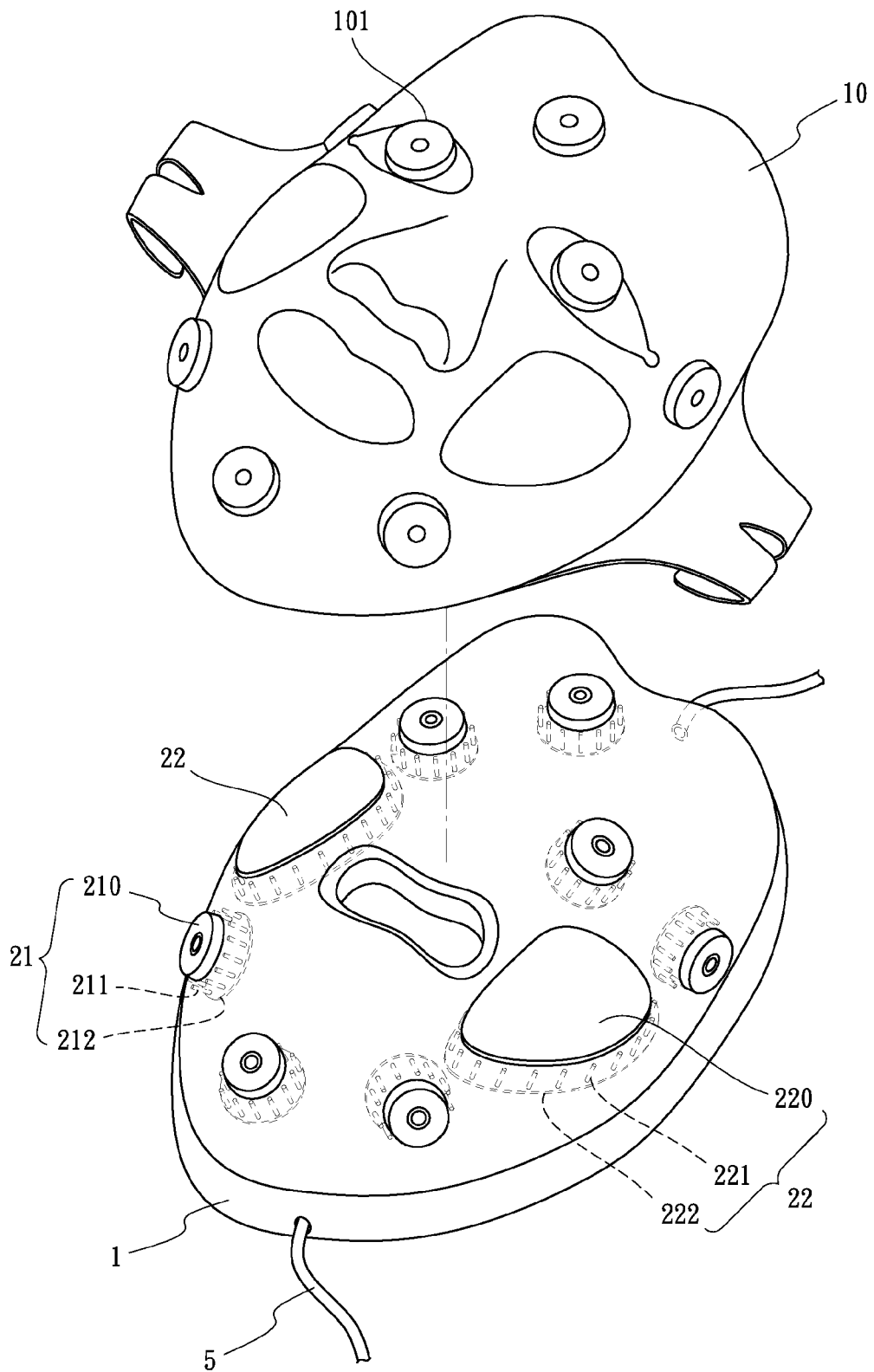
FIG. 2 is an exploded perspective view of the mask of the therapeutic appliance shown in FIG. 1.
Figure 3:
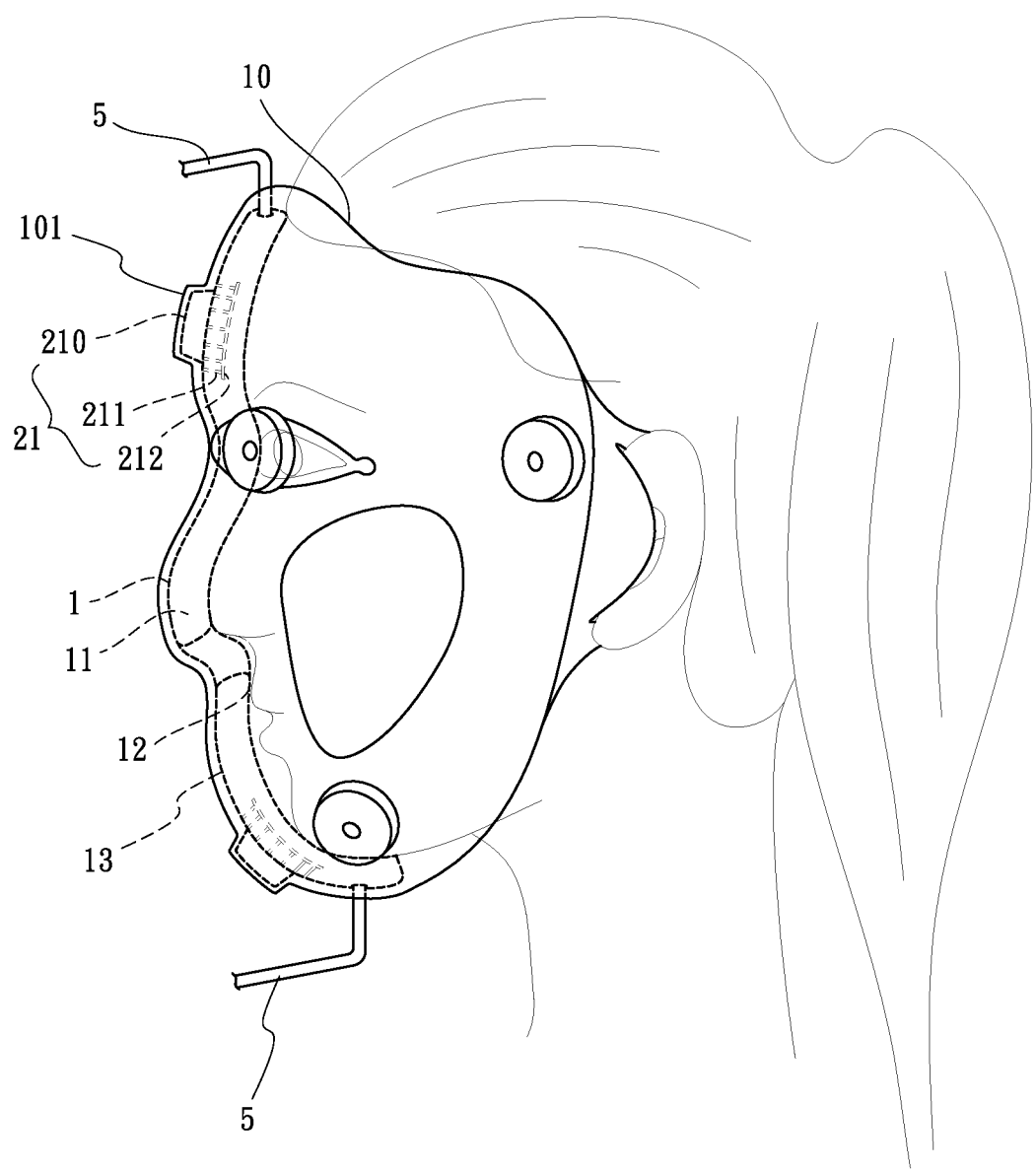
FIG. 3 illustrates the mask of the therapeutic appliance is applied onto the face of the user for facial treatment.
Figure 4:
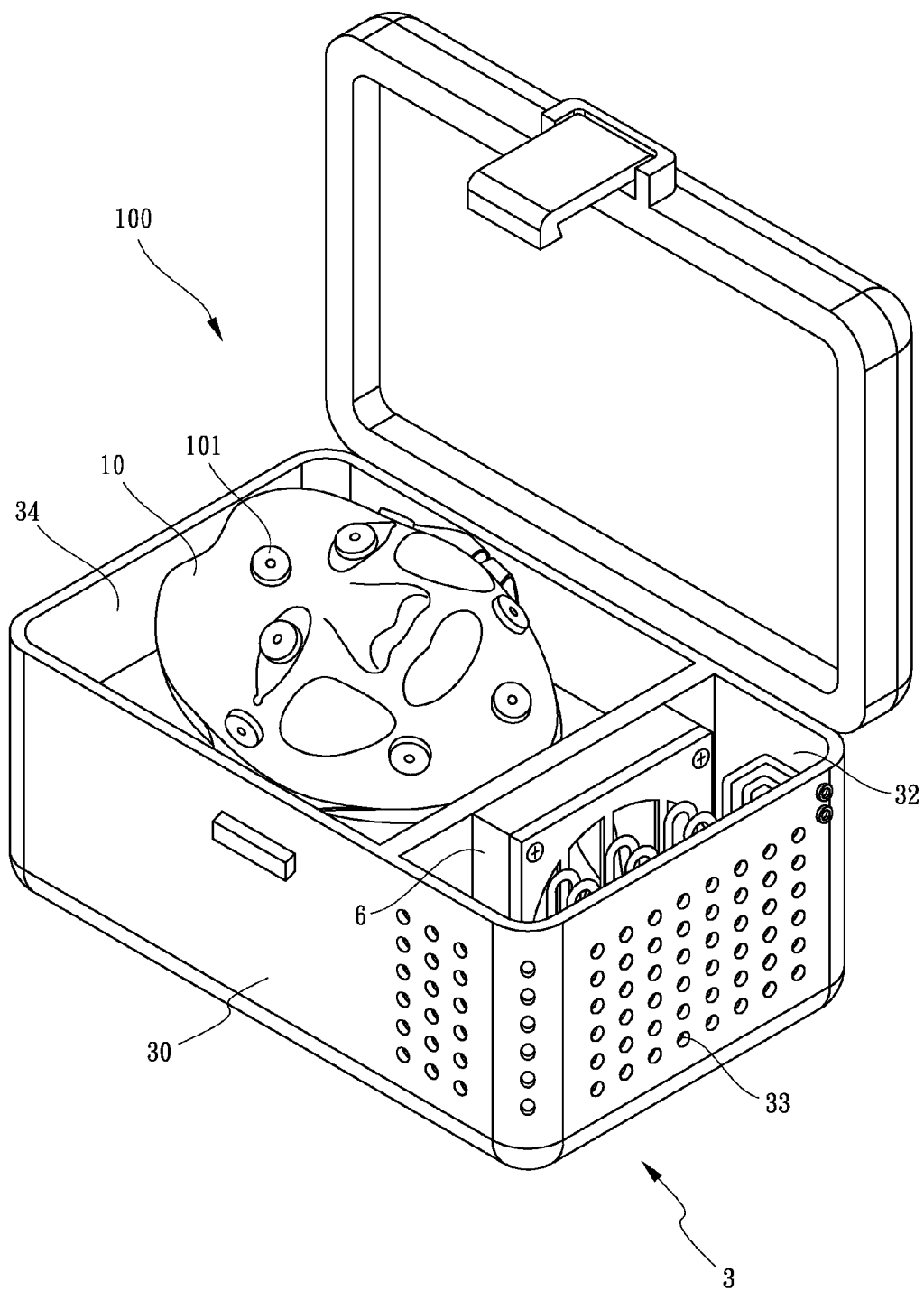
FIG. 4 a perspective view of the therapeutic appliance with the mask stored in a carrying case thereof.

Referring to now to FIGS. 1-7, there is shown a therapeutic appliance 100 (see FIG. 4) embodying the present invention and generally comprising a hot and cold eye mask (see FIG. 1), a recirculating water system 3 (see FIG. 5 or 6) detachably connected to the eye mask, and a thermoelectric device 4 (see FIG. 4). The eye mask generally includes a water pack 1, a rigid covering 10 placed over the water pack 1, and a plurality of massaging fingers 21, 22 of different sizes.

With reference to FIGS. 2 and 3, the water pack 1 has a cavity 11 for containing a liquid. Each of the massaging fingers 21 or 22 has a vibrator 210, 220, a buffering base 212, 222 and a plurality of flexible ribs 211, 221. The vibrators 210, 220 are disposed on the water pack 1 to excite the liquid in the water pack 1 for massaging a body portion to be massaged. Specifically, the water pack 1 has one side 12 to be in contact with the body portion and the opposite side 13 on which the vibrators 210, 220 of the massaging fingers 21, 22 are mounted. Each of the flexible ribs 211, 221 has one end extending from a periphery of the buffering base 212, 222 and the other end attached, to an internal wall surface of the water pack 1 such that the ribs 211, 221 are arranged in a shape generally conforming to a contour of the vibrator 210, 220. With the buffering base 212, 222 and the flexible ribs 211, 221, each of the massaging fingers 21, 22 can provide a relatively small but comfortable massage to the user using the therapeutic appliance 100.

Preferably, a rigid covering 10 may be employed to be placed over the water pack 1 as well as the massaging fingers 21, 22 for protection. More preferably, the covering 10 may be shaped to form a plurality of receptacles 101 receive the respective vibrators 210.

Figure 6:
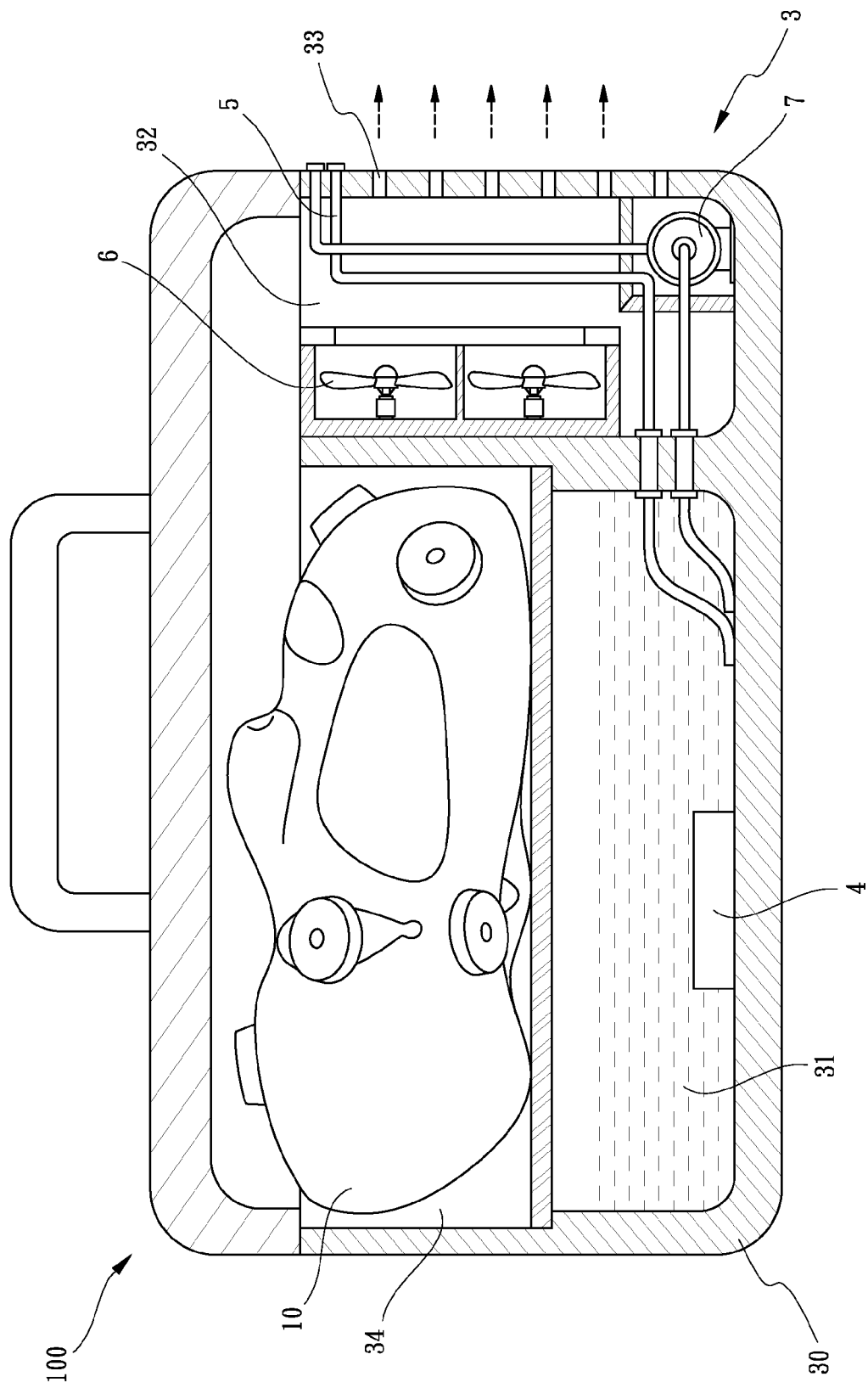
FIG. 6 a cross sectional view of the therapeutic appliance, taken along the line VI-VI.
Figure 7:
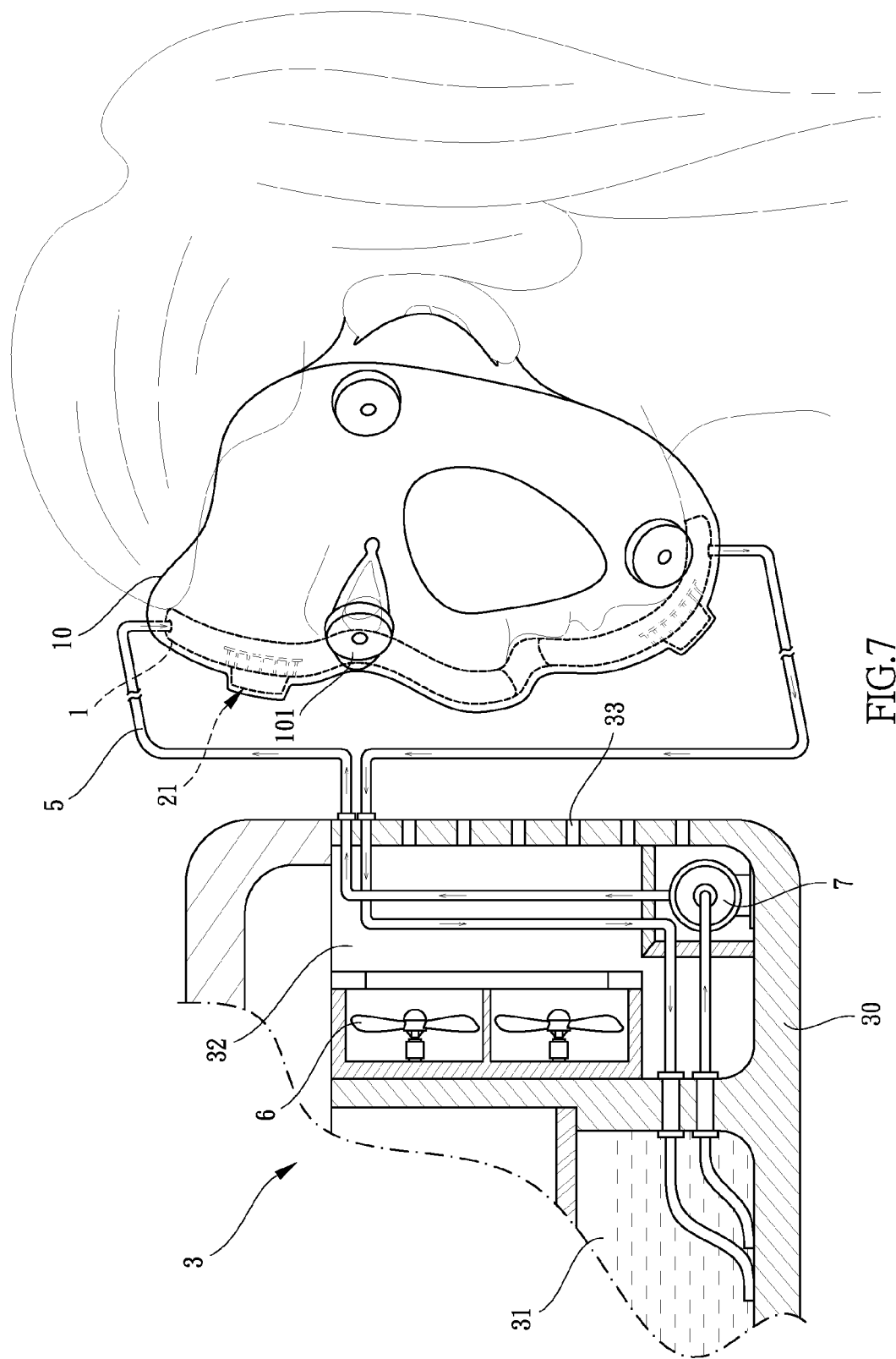
FIG. 7 illustrates a state when the therapeutic appliance is in use.

Referring to FIGS. 6 and 7, the recirculating water system 3 has a container 30, a conduit 5 connecting the container 30 and the water pack 1, and at least one cooling fan 6. The container 30 is divided into a first compartment 31 in which the liquid, is stored, a second compartment 34 in which the eye mask can be stored when not in use (see FIG. 4 or 6), and a third compartment 32 in which the conduit 5 is partially disposed. The first compartment 31 is in communication with the chamber 11 of the water pack 1 via the conduit 5.

The thermoelectric device 4 is disposed in the first compartment 31 of the container 30 of the recirculating water system 3 for heating or cooling liquid circulating between the water pack 1 and the container 30. That is, the thermoelectric device 4 acts to achieve a preselected temperature for the liquid in the water pack 1. Moreover, a pump 7 is employed in the third compartment 32 for forcing the liquid to flow through the conduit 5 and between the first compartment 31 of the container and the cavity 11 of the water pack 1 so that the liquid is permitted to circulate between the container 30 and the water pack 1. Thus, heating or cooling of the liquid is accomplished by heating or cooling the liquid outside the eye mask and supplying the heated or cooled liquid to the water pack 1 by the conduit 5. Safety for the user of the therapeutic appliance 100 is therefore enhanced by positioning the thermoelectric device 4 in the container 30, sufficiently isolated from the eye mask.

The cooling fan 6 is disposed in the third compartment 32 and is directed toward the conduit 5 for heat dissipation. Preferably, a plurality of vent holes 33 are defined in a wall of the third compartment 32 for circulation of air.

Figure 5:
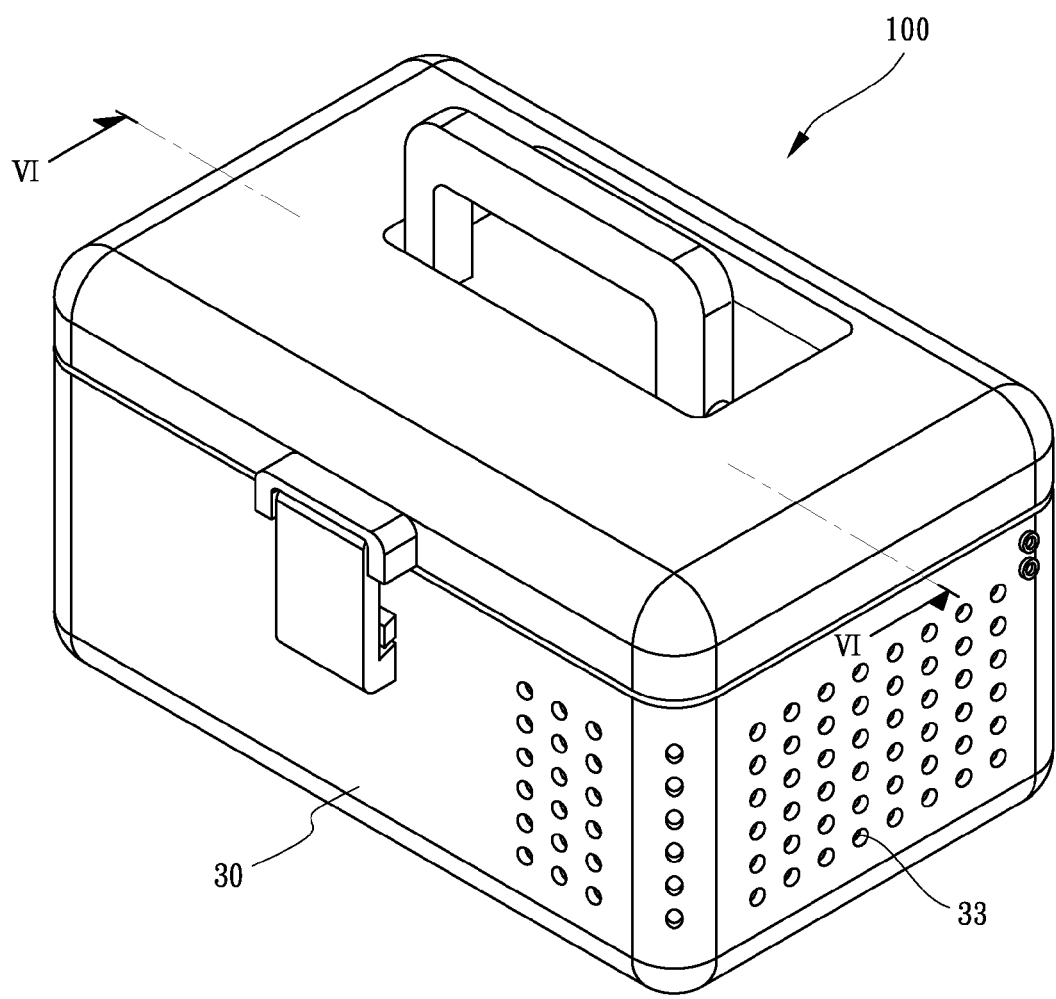
FIG. 5 another perspective view of the therapeutic appliance with its carrying case closed.

For ease of carrying, the container 30 of the recirculating water system 3 may be formed in a box-like carrying case, as depicted in FIG. 4 or 5. Flexibility for the user of the therapeutic appliance 100 is enhanced by removably connecting the recirculating water system 3 to the eye mask.

Figure 8:
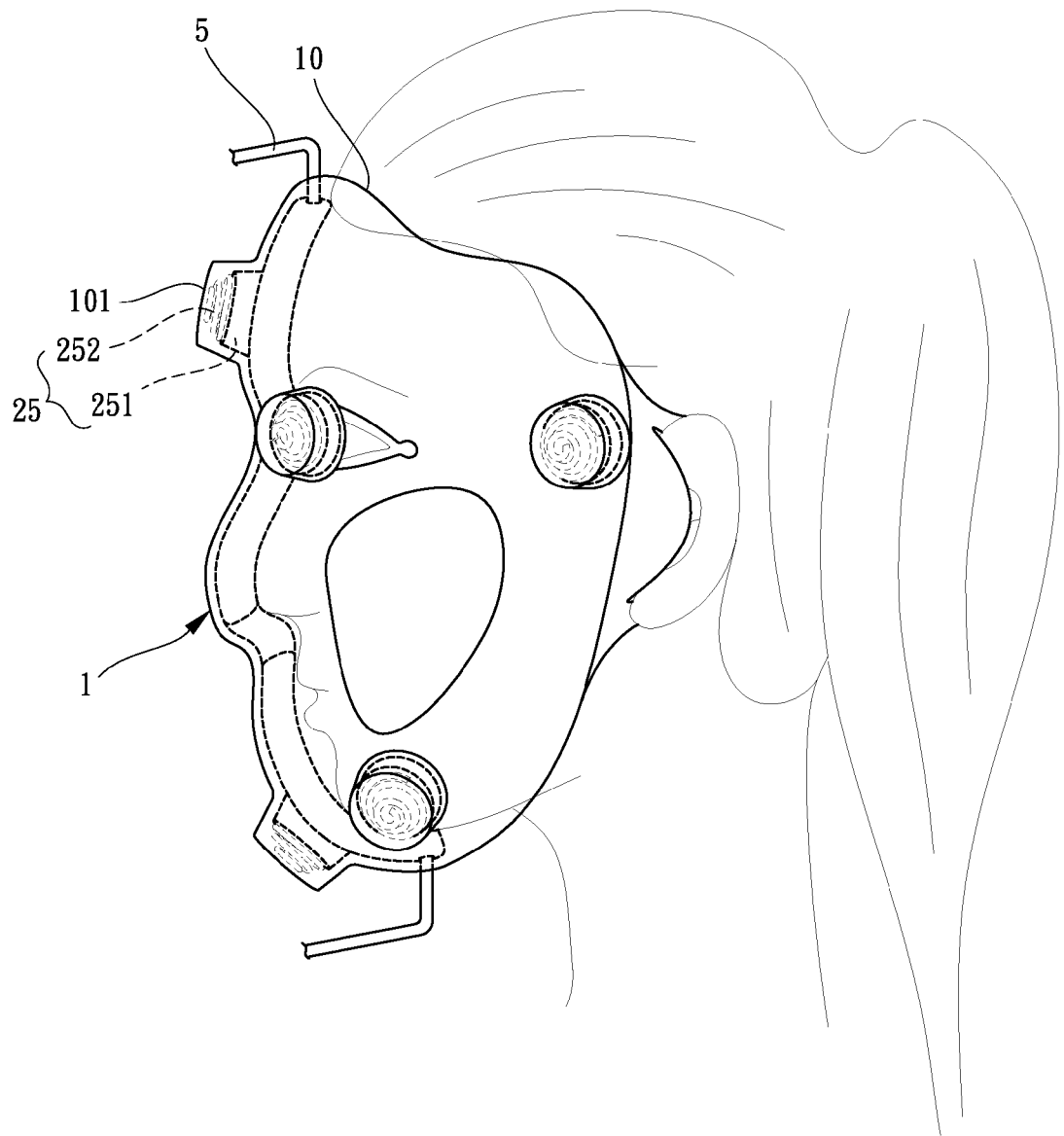
FIG. 8 is a view similar to FIG. 3 except that the massaging finger of the mask is modified.

Referring now to FIG. 8, there is shown an alternate embodiment of the eye mask, which is similar to that of FIG. 3, except that in each relatively smaller massaging finger 25, a spring 252 is provided in lieu of the buffering base 212 and the flexible ribs 211 of each massaging finger 21. The spring 252 is interposed in between the associated receptacle 101 of the covering 10 and the associated vibrator 251 of the massaging finger 25. Similarly, the massaging fingers 25 can provide a comfortable massage to the body portion.

Figure 9:
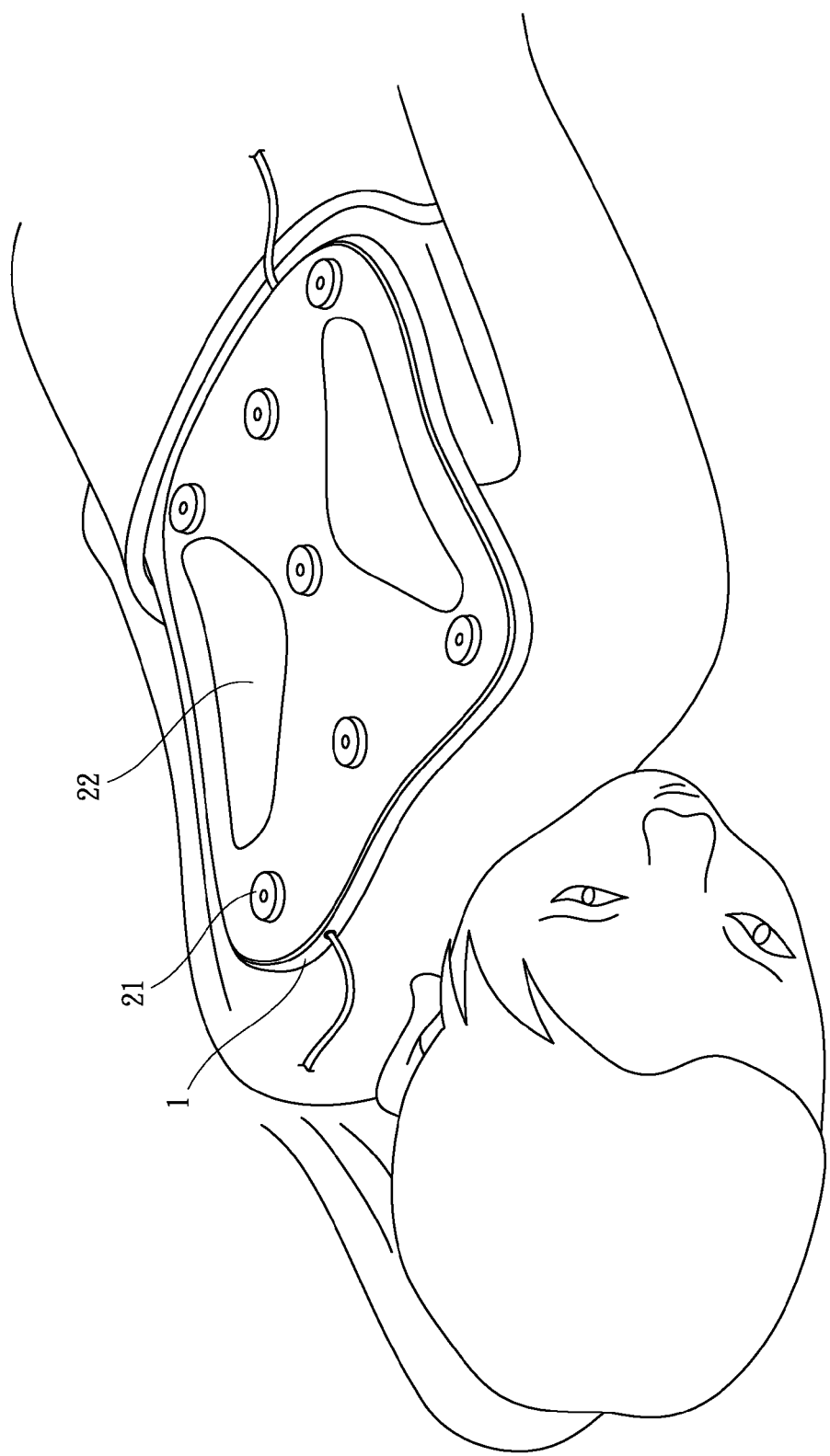
FIG. 9 illustrates a modified water pack shaped to be applied onto the back of the user.
Figure 10:
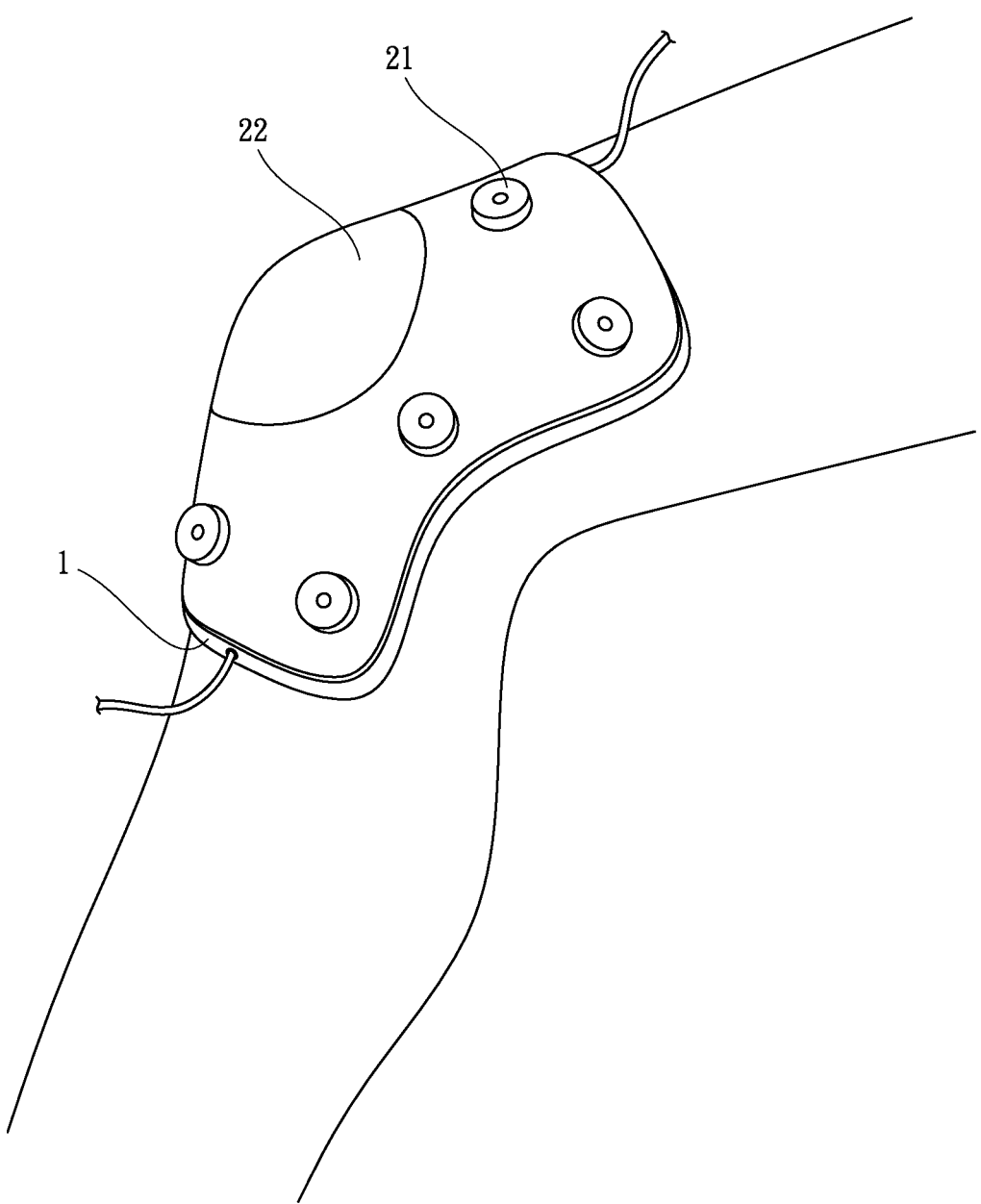
FIG. 10 illustrates another modified water pack shaped to be applied onto a knee of the user.

It is understood that the preferred embodiment of the present invention is applied for a facial treatment in which the water pack 1 of the therapeutic appliance 100 is placed on the face of the user. Alternately, in other embodiments, such a technique can also be used if devices for other than the face of the user are constructed within the principles of the present invention. For instance, an apparatus which is attached to the back of the user, as illustrated in FIG. 9, or the knee of the user, as illustrated in FIG. 10 can be employed.

It is to be understood that the disclosed embodiments are illustrative in nature and the invention is not to be limited to any one or more embodiments except as set forth in the following claims.

What is claimed is:

1. A therapeutic appliance comprising:
    a water pack for containing a liquid;
    at least one massaging finger having a vibrator disposed on the water pack to excite the liquid in the water pack for being adapted to massage a body portion, the water pack having one side adapted to be in contact with the body portion and the opposite side on which the vibrator is mounted, the at least one massaging finger including a buffering base and a plurality of flexible ribs, each flexible rib having one end extending from a periphery of the buffering base, and the other end of each flexible rib attached to an internal wall surface of the water pack such that the flexible ribs are arranged in a shape generally conforming to a contour of the vibrator;
    a recirculating water system having a container and a conduit connecting the container and the water pack such that the liquid is permitted to circulate between the container and the water pack; and
    a thermoelectric device disposed in the container of the recirculating water system for heating or cooling the liquid.

2. The therapeutic appliance of claim 1, further comprising a rigid covering generally placed over the water pack as well as the massaging finger.

3. The therapeutic appliance of claim 1, wherein the container of the recirculating water system defines:
    a first compartment in communication with a chamber of the water pack via the conduit and in which the liquid is stored; and
    a second compartment in which the water pack along with the massaging finger is stored when not in use.

4. The therapeutic appliance of claim 3, wherein the container of the recirculating water system further defines a third compartment in which the conduit is partially disposed; and the recirculating water system further includes at least one cooling fan disposed in the third compartment and directed toward the conduit for heat dissipation.

5. The therapeutic appliance of claim 4, wherein the recirculating water system further includes a pump disposed in the third compartment for forcing the liquid to flow through the conduit and between the container and the water pack.

6. The therapeutic appliance of claim 4, wherein the container defines a plurality of vent holes in a wall of the third compartment.

* * * * *